United States Patent
Chen et al.

(10) Patent No.: US 9,034,688 B2
(45) Date of Patent: *May 19, 2015

(54) ANTIMONY COMPOUNDS USEFUL FOR DEPOSITION OF ANTIMONY-CONTAINING MATERIALS

(71) Applicant: Advanced Technology Materials, Inc., Danbury, CT (US)

(72) Inventors: Tianniu Chen, Rocky Hill, CT (US); William Hunks, Waterbury, CT (US); Philip S. H. Chen, Bethel, CT (US); Chongying Xu, New Milford, CT (US); Leah Maylott, Farmington, CT (US)

(73) Assignee: ENTEGRIS, INC., Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/217,866

(22) Filed: Mar. 18, 2014

(65) Prior Publication Data

US 2014/0206136 A1    Jul. 24, 2014

Related U.S. Application Data

(63) Continuation of application No. 12/990,459, filed as application No. PCT/US2009/042290 on Apr. 30, 2009, now Pat. No. 8,674,127.

(60) Provisional application No. 61/050,111, filed on May 2, 2008.

(51) Int. Cl.
| | |
|---|---|
| C07F 9/90 | (2006.01) |
| H01L 21/02 | (2006.01) |
| C23C 16/18 | (2006.01) |
| C07C 211/65 | (2006.01) |
| H01L 45/00 | (2006.01) |

(52) U.S. Cl.
CPC ........ *H01L 21/02568* (2013.01); *C07C 211/65* (2013.01); *C07F 9/902* (2013.01); *C07F 9/908* (2013.01); *H01L 45/06* (2013.01); *H01L 45/144* (2013.01); *H01L 45/1616* (2013.01); *C23C 16/18* (2013.01)

(58) Field of Classification Search
CPC . H01L 21/02568; H01L 45/06; H01L 45/144; C07F 9/902; C07F 9/904; C07F 9/908; C07C 211/65; C23C 16/18
USPC ............ 556/64, 70; 438/102; 106/285, 287.1, 106/287.18
See application file for complete search history.

(56) References Cited

U.S. PATENT DOCUMENTS

| | | |
|---|---|---|
| 4,960,916 A | 10/1990 | Pazik |
| 5,596,522 A | 1/1997 | Ovshinsky et al. |
| 6,005,127 A | 12/1999 | Todd et al. |
| 6,146,608 A | 11/2000 | Todd et al. |
| 6,281,022 B1 | 8/2001 | Li et al. |
| 6,750,079 B2 | 6/2004 | Lowrey et al. |
| 6,767,830 B2 | 7/2004 | Wang et al. |
| 7,115,927 B2 | 10/2006 | Hideki et al. |
| 7,371,429 B2 | 5/2008 | Lee et al. |
| 7,397,060 B2 | 7/2008 | Lung |
| 7,425,735 B2 | 9/2008 | Park et al. |
| 7,488,967 B2 | 2/2009 | Burr et al. |
| 7,569,417 B2 | 8/2009 | Lee et al. |
| 8,674,127 B2 | 3/2014 | Chen et al. |
| 2004/0012009 A1 | 1/2004 | Casagrande et al. |
| 2004/0197945 A1 | 10/2004 | Woelk et al. |
| 2005/0029502 A1 | 2/2005 | Hudgens |
| 2005/0267345 A1 | 12/2005 | Korgel et al. |
| 2006/0035462 A1 | 2/2006 | Millward |
| 2006/0049447 A1 | 3/2006 | Lee et al. |
| 2006/0138393 A1 | 6/2006 | Seo et al. |
| 2006/0141710 A1 | 6/2006 | Yoon et al. |
| 2006/0172067 A1 | 8/2006 | Ovshinsky et al. |
| 2006/0172083 A1 | 8/2006 | Lee et al. |
| 2007/0090336 A1 | 4/2007 | Asano et al. |
| 2007/0121363 A1 | 5/2007 | Lung |
| 2007/0160760 A1 | 7/2007 | Shin et al. |
| 2007/0246748 A1 | 10/2007 | Breitwisch et al. |
| 2008/0035906 A1 | 2/2008 | Park et al. |
| 2008/0035961 A1 | 2/2008 | Chen et al. |

(Continued)

FOREIGN PATENT DOCUMENTS

| | | |
|---|---|---|
| JP | 58-38296 A | 3/1983 |
| JP | 5-311423 A | 11/1993 |

(Continued)

OTHER PUBLICATIONS

Stauf, G., et al., "Low Temperature ALD of Germanium for Phase Change Memory Thin Films", "AVS 7th International Conference on Atomic Layer Deposition—ALD 2007", Jun. 24, 2007, pp. 18.
Wu, L., et al., "Humidity Sensitivity of Sr(Sn, Ti)03 Ceramics", "Journal of Electronic Materials", 1990, pp. 197-200, vol. 19, No. 2.
Abrutis, A., et al., "Hot-Wire Chemical Vapor Deposition of Chalcogenide Materials for Phase Change Memory Applications", "Chem. Mater.", May 2008, pp. 3557-3559, vol. 20, No. 11.
Auner, N., et al, "Organosilicon Chemistry IV: From Molecules to Materials", Mar. 2000, p. 291 (Abstract), Publisher: Wiley-Vch.

(Continued)

*Primary Examiner* — Porfirio Nazario Gonzalez
(74) *Attorney, Agent, or Firm* — Hultquist, PLLC; Mary B. Grant; Maggie Chappuis

(57) ABSTRACT

Precursors for use in depositing antimony-containing films on substrates such as wafers or other microelectronic device substrates, as well as associated processes of making and using such precursors, and source packages of such precursors. The precursors are useful for deposition of $Ge_2Sb_2Te_5$ chalcogenide thin films in the manufacture of nonvolatile Phase Change Memory (PCM) or for the manufacturing of thermoelectric devices, by deposition techniques such as chemical vapor deposition (CVD) and atomic layer deposition (ALD).

20 Claims, 4 Drawing Sheets

(56) References Cited

U.S. PATENT DOCUMENTS

| | | |
|---|---|---|
| 2008/0078984 A1 | 4/2008 | Park et al. |
| 2008/0118636 A1 | 5/2008 | Shin et al. |
| 2008/0210163 A1 | 9/2008 | Carlson et al. |
| 2008/0254218 A1 | 10/2008 | Lei et al. |
| 2008/0290335 A1 | 11/2008 | Lin et al. |
| 2009/0020738 A1 | 1/2009 | Happ et al. |
| 2009/0087561 A1 | 4/2009 | Chen et al. |
| 2009/0101883 A1 | 4/2009 | Lai et al. |
| 2009/0112009 A1 | 4/2009 | Chen et al. |
| 2009/0124039 A1 | 5/2009 | Roeder et al. |
| 2009/0215225 A1 | 8/2009 | Stender et al. |
| 2009/0227066 A1 | 9/2009 | Joseph et al. |
| 2009/0275164 A1 | 11/2009 | Chen et al. |
| 2009/0291208 A1 | 11/2009 | Gordon et al. |
| 2009/0298223 A1 | 12/2009 | Cheek et al. |
| 2009/0305458 A1 | 12/2009 | Hunks et al. |
| 2009/0321733 A1 | 12/2009 | Gatineau et al. |
| 2010/0012917 A1 | 1/2010 | Takaura et al. |
| 2010/0018439 A1 | 1/2010 | Cameron et al. |
| 2010/0054029 A1 | 3/2010 | Happ et al. |
| 2010/0190341 A1 | 7/2010 | Park et al. |
| 2010/0270527 A1 | 10/2010 | Sawamura |
| 2011/0001107 A1 | 1/2011 | Zheng |
| 2011/0060165 A1 | 3/2011 | Cameron et al. |
| 2011/0065252 A1 | 3/2011 | Nakamura |
| 2011/0124182 A1 | 5/2011 | Zheng |
| 2011/0227021 A1 | 9/2011 | Schrott et al. |
| 2011/0260132 A1 | 10/2011 | Zheng et al. |

FOREIGN PATENT DOCUMENTS

| | | |
|---|---|---|
| JP | 2001-67720 A | 3/2001 |
| JP | 2002-211924 A | 7/2002 |
| JP | 2002-220658 A | 8/2002 |
| JP | 2006-511716 A | 4/2006 |
| JP | 2006-124262 A | 5/2006 |
| JP | 2006-182781 A | 7/2006 |
| JP | 2011-66135 A | 3/2011 |
| KR | 10-2004-0076225 A | 8/2004 |
| KR | 10-2005-0048891 A | 5/2005 |
| KR | 10-2006-0091160 A | 8/2006 |
| KR | 10-2007-0025612 A | 3/2007 |
| KR | 10-0695168 B1 | 3/2007 |
| KR | 10-2007-0105752 A | 10/2007 |
| KR | 10-2008-0052362 A | 6/2008 |
| KR | 10-2008-0080273 A | 9/2008 |
| KR | 10-2009-0008799 A | 1/2009 |
| TW | 200821403 A | 5/2008 |
| WO | 2004046417 A2 | 6/2004 |
| WO | 2005084231 A2 | 9/2005 |
| WO | 2006012052 A2 | 2/2006 |
| WO | 2007070218 A2 | 6/2007 |
| WO | 2008057616 A2 | 5/2008 |
| WO | 2009034775 A1 | 3/2009 |

OTHER PUBLICATIONS

Cheng, H., et al., "Wet Etching of GE2SB2TE5 Films and Switching Properties of Resultant Phase Change Memory Cells", "Semiconductor Science and Technology", Sep. 26, 2005, pp. 1111-1115, vol. 20, No. 11.

Christen, H., et al, "Semiconducting epitaxial films of metastable SrRu0.5Sn0.5O3 grown by pulsed laser deposition", "Applied Physics Letters", 1997, pp. 2147-2149 (Title and Abstract), vol. 70, No. 16.

Gupta, A., et al., "Triorganoantimony(V) complexes with internally functionallized oximes: synthetic, spectroscopic and structural aspects of [R3Sb(Br)L], [R3Sb(OH)L] and [R3SbL2], crystal and molecular structures of [Me3Sb{ON=C (Me)C4H3O}2], [Me3Sb{on=C(Me)C4H3S}2], 2-OC4H3C(Me)=NOH and 2-SC4H3C(Me)=NOH", "Journal of Organometallic Chemistry", 2002, pp. 118-126, vol. 645.

Horii, H., et al, "A Novel Cell Technology Using N-Doped Gesbte Films for Phase Change Ram", "Symposium on VLSI Technology Digest of Technical Papers", Jun. 10-12, 2003, pp. 177-178.

Karsch, H., et al., "Bis(annidinate) Complexes of Silicon and Germanium", "Eur. J. Inorg. Chemistry", Apr. 1998, pp. 433-436, vol. 4.

Kim, R., et al., "Structural properties of Ge2Sb2Te5 thin films by metal organic chemical vapor deposition for phase change memory applications", "Applied Physics Letters", Sep. 6, 2006, pp. 1021071-1021073, vol. 89.

Kissounko, D., et al., "Principal trends in the chemistry of amidinate complexes of main-group and transition elements", "Russian Chemical Reviews", May 1, 2006, pp. 351-374, vol. 75, No. 5.

Kvyatkovskii, O., "On the Nature of Ferroelectricity in Sr1-xAxTiO3 and KTa1-xNbxO3 Solid Solutions", "Physics of the Solid State", 2002, pp. 1135-1144, vol. 44, No. 6.

Lee, J., et al., "GeSbTe deposition for the PRAM application", "Applied Surface Science", Feb. 2007, pp. 3969-3976, vol. 253, No. 8.

Lu, H., et al., "Evolution of itinerant ferromagnetism in SrxPb1-xRuO3 (0 less than or equal to x less than or equal to 1): Interplay between Jahn-Teller distortion and A-site disorder", "Applied Physics Letters", Mar. 22, 2011, pp. 13, vol. 98, No. 122503.

Niinistoe, J., et al., "Atomic Layer Deposition of High-k Oxides of the Group 4 Metals for Memory Applications", "Advanced Engineering Materials", Mar. 9, 2009, pp. 223-234, vol. 11, No. 4.

Raj, P., et al., "Synthesis and characterization of the complex triorganoantimony (V) cations, R3SbL'2+and R3Sb (L-L)2+", "Synthesis and Reactivity in Inorganic and Metal-Organic Chemistry", 1992, pp. 543-557 (Abstract), vol. 22, No. 5.

Raj, P., et al., "Synthesis and geometry of complex triorganoantimony(V) cations", "Synthesis and Reactivity in Inorganic and Metal-Organic Chemistry", 1992, pp. 1471-1494 (Abstract), vol. 22, No. 10.

ANTIMONY COMPOUNDS USEFUL FOR DEPOSITION OF ANTIMONY-CONTAINING MATERIALS

CROSS-REFERENCE TO RELATED APPLICATION

This application is a continuation application of U.S. patent application Ser. No. 12/990,459, filed Oct. 29, 2010, issued as U.S. Pat. No. 8,674,127, which application is a U.S. national phase under the provisions of 35 U.S.C. §371 of International Patent Application No. PCT/US09/42290 filed Apr. 30, 2009, which in turn claims the benefit of priority under 35 U.S.C. §119(e) of U.S. Provisional Patent Application No. 61/050,111 filed on May 2, 2008. The disclosures of such nonprovisional patent application, international patent application and U.S. provisional application are hereby incorporated herein by reference in their respective entireties, for all purposes.

FIELD OF THE INVENTION

The present invention relates to precursors for use in depositing antimony-containing films on substrates such as wafers or other microelectronic device substrates, as well as associated processes of making and using such precursors, and source packages of such precursors.

DESCRIPTION OF THE RELATED ART

In the manufacture of microelectronic devices, there is emerging interest in the deposition of $Ge_2Sb_2Te_5$ chalcogenide thin films for nonvolatile Phase Change Memory (PCM), due to its relatively easy integration pathways with silicon-based integrated circuits. Chemical vapor deposition (CVD) and atomic layer deposition (ALD) processing of these materials are of primary interest as deposition techniques for advanced device applications.

The anticipated use of high aspect ratio geometries in PCMs and the corresponding requirement to achieve smooth films of proper phase and non-segregated character, require processes that are efficient in forming high-quality antimony-containing films at low temperatures (<400° C.). Suitable antimony precursors are required that are compatible with such requirements, and that preferably have high volatility at standard temperature and pressure conditions.

SUMMARY OF THE INVENTION

The present invention relates to antimony precursors useful for depositing antimony-containing films on substrates such as wafers or other microelectronic device substrates, as well as associated processes of making and using such precursors, and source packages of such precursors.

In one aspect, the invention relates to an antimony precursor selected from among the following general classes:

Class I

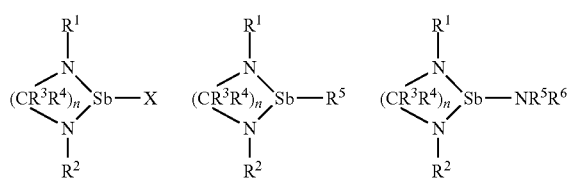

Class II

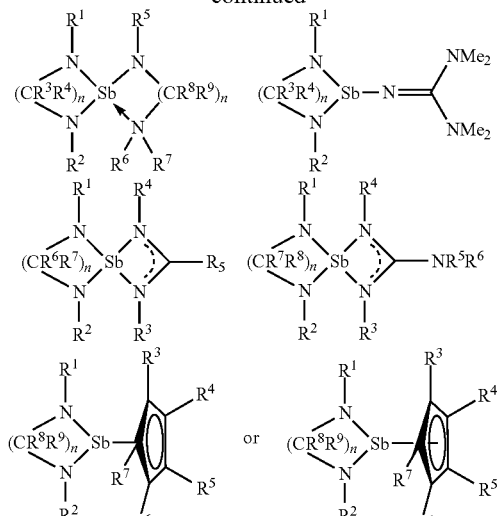

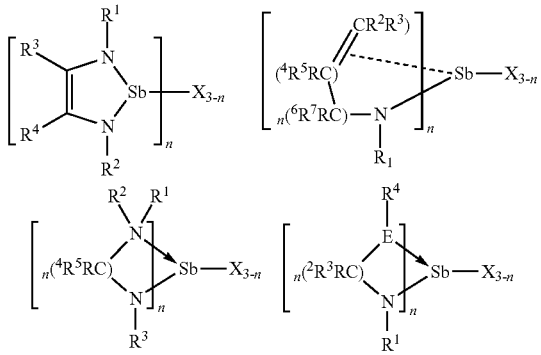

wherein:

each of R, $R^1$, $R^2$, $R^3$, $R^4$, $R^5$, $R^6$, $R^7$, $R^8$, and $R^9$ is the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl;

X is the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl, amidinate, guanidinate, isourate, cyclopentadienyl ($C_5R_5$); and n is an integer from 1 to 7, e.g., from 1 to 6.

Specific compounds within these general formulae include the following:

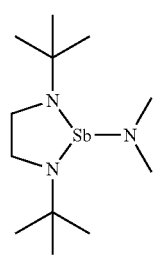

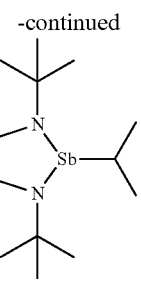

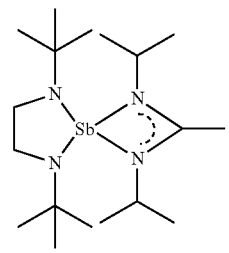

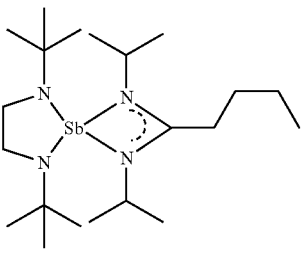

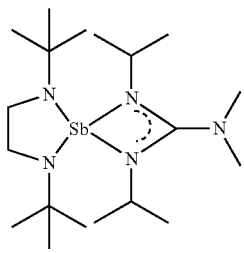

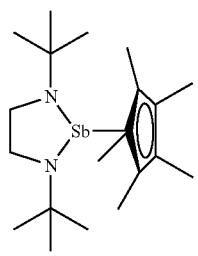

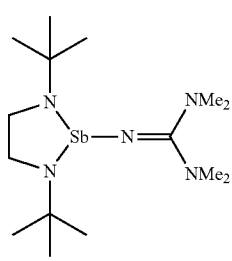

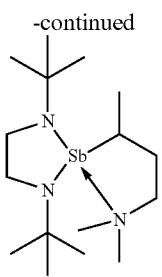

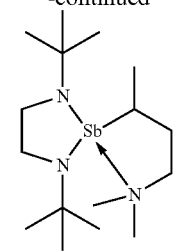

The antimony-containing precursors can be included in a composition comprising: the antimony-containing precursor and a solvent medium in which the compound is dissolved.

A further aspect of the invention relates a precursor vapor comprising vapor of an antimony-containing precursor described above.

The antimony-containing precursors can be used to deposit an antimony-containing film on a substrate. The method for depositing the film comprises volatilizing an antimony-containing precursor to form a precursor vapor, and contacting the substrate with the precursor vapor under deposition conditions to form the antimony-containing film on the substrate. The antimony-containing precursors have one of the formulae described above.

A further aspect of the invention relates to a packaged precursor, comprising a precursor storage and vapor dispensing vessel having disposed therein an antimony-containing precursor with the formula described above.

The antimony-containing precursors can be used as the antimony component to form a GST film on a substrate, by depositing the antimony-containing precursors, along with one or more germanium and tellurium-containing precursors, on the substrate from a vapor comprising the precursor.

The precursors can also be used to form PCRAM devices, by forming a GST film on a substrate for fabrication of said device. The forming step comprises depositing the antimony-containing precursors, along with germanium and tellurium-containing precursors, on the substrate from a vapor comprising the precursors.

The antimony-containing precursors can be present in a composition comprising the antimony-containing precursor and a solvent medium in which said compound is dissolved.

The antimony-containing precursors can be prepared, for example, using a process as described below:

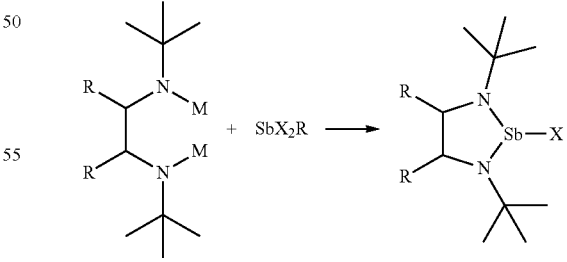

wherein
X is halogen,
M is Li, Na, or K, and
each R is, independently,
the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl, amidinate —C(NR$_2$)(NR$_3$)R$_4$, guanidinate —C(NR$_2$)(NR$_3$)NR$^4$R$^5$, isourate, cyclopendienyl (C$_5$R$_5$), and guanidinate (—N=C—(NMe$_2$)$_2$).

When preparing the compounds, it alternatively may be advantageous to start with an antimony trihalide, then form the ring as described above, leaving a single halogen on the antimony. This halogen can be reacted with an anionic reagent such as lithium-cyclopentadienide compound to form the desired products. This reaction scheme is outlined below:

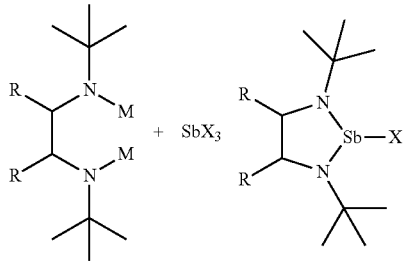

wherein

M=Li, Na, or K;

X=Cl, Br, or I;

each of R$^1$, R$^2$, R$^3$ and R$^4$ is the same as or different from others, and each is independently selected from H, C$_1$-C$_6$ alkyl, C$_1$-C$_6$ alkoxy, C$_3$-C$_8$ cycloalkyl, C$_6$-C$_{10}$ aryl, silyl, substituted silyl, aminoalkyl, alkoxyalkyl, aryloxyalkyl, imidoalkyl and acetylalkyl.

Another synthetic approach is to react the neutral diamine directly with an antimony trihalide in the presence of a base to scavenge the liberated HCl according to the scheme below:

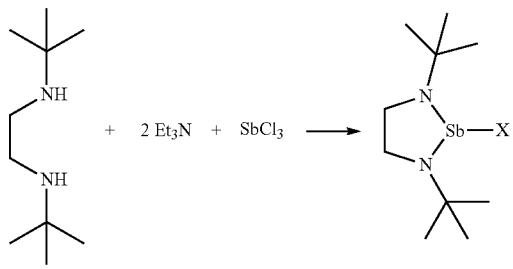

Then, the resulting compound can be reacted with a cyclopentadienyl anion to form compounds of the formula:

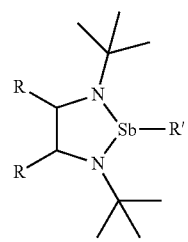

wherein the R' group attached to the antimony atom is a cyclopentadienyl moiety, as shown below:

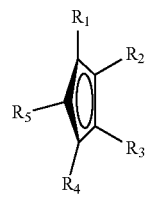

Where R$_{1-4}$ are as described above, and wherein the attachment to the Sb can result in either σ- or π-bonded complexes as illustrated by the following specific compounds:

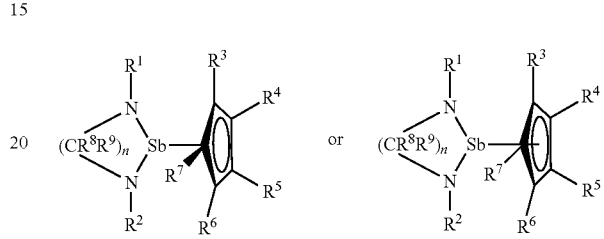

A still further aspect of the invention relates to a precursor vapor comprising vapor of an antimony precursor as described above.

Another aspect of the invention relates to a method of depositing an antimony-containing film on a substrate, comprising volatilizing an antimony precursor as described herein to form a precursor vapor, and contacting the substrate with the precursor vapor under deposition conditions to form the antimony-containing film on the substrate, wherein said antimony precursor is selected from the group consisting of:

Class I

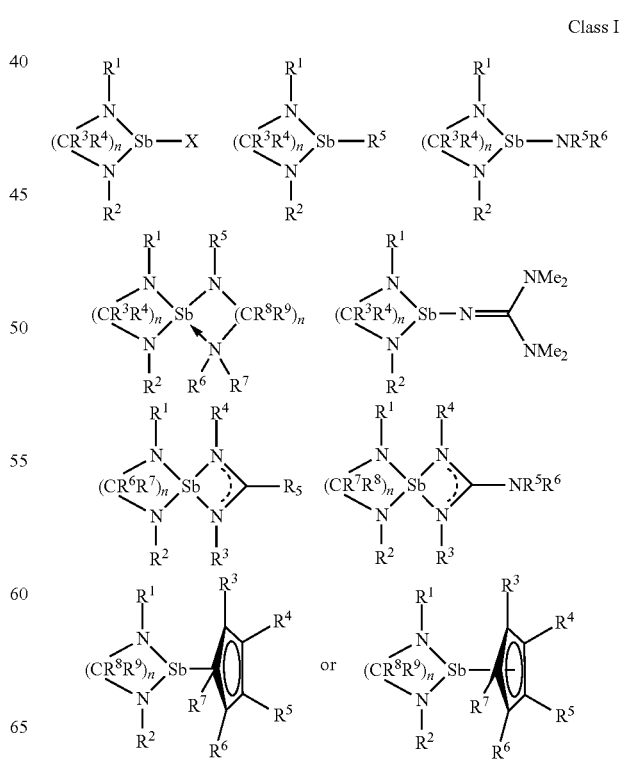

-continued

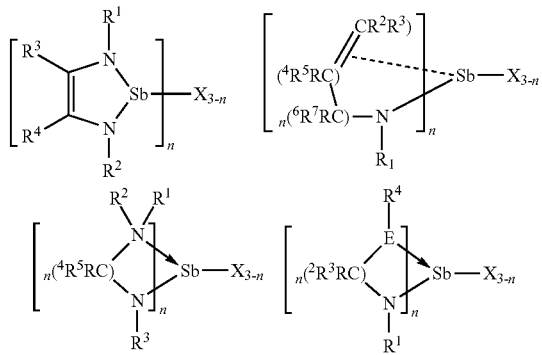

Class II wherein:
each of R, $R^1$, $R^2$, $R^3$, $R^4$, $R^5$, $R^6$, $R^7$, $R^8$, and $R^9$ is the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl;

X is the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl, amidinate, guanidinate, isourate, cyclopentadienyl ($C_5R_5$); and n is an integer of from 1 to 7, e.g., from 1 to 6.

A further aspect of the invention relates to a packaged precursor, comprising a precursor storage and vapor dispensing vessel having disposed therein an antimony precursor as described above.

A further aspect of the invention relates to a method of forming a GST film on a substrate, comprising depositing antimony on the substrate from vapor of an antimony precursor as described above.

The invention in another aspect relates to a method of making a PCRAM device, comprising forming a GST film on a substrate for fabrication of said device, wherein said forming comprises depositing antimony on the substrate from vapor of an antimony precursor selected from among the above described.

The precursors can be used to form a GST film on a substrate, by depositing one or more of the antimony-containing precursors described herein along with one or more germanium and tellurium-containing precursors on the substrate from a vapor comprising the precursors.

The precursors can also be used to form PCRAM devices, by forming a GST film on a substrate for fabrication of said device as described above.

In one aspect, the invention further relates to a method of combating pre-reaction of precursors described herein in a vapor deposition process for forming a film on a substrate, wherein the precursors described herein are susceptible to pre-reaction adversely affecting the film. In this aspect, the method involves introducing to the process a pre-reaction-combating agent selected from the group consisting of (i) heteroatom (O, N, S) organo Lewis base compounds, (ii) free radical inhibitors, and (iii) deuterium-containing reagents.

Another aspect of the invention relates to a method of combating pre-reaction of the precursors described in a vapor deposition process in which multiple feed streams are flowed to a deposition locus to form a film on a substrate, wherein at least one of said multiple feed streams includes a precursor susceptible to pre-reaction adversely affecting the film. The method involves introducing to at least one of said multiple feed streams or supplied materials therefor, or to the deposition locus, a pre-reaction-combating agent selected from the group consisting of (i) heteroatom (O, N, S) organo Lewis base compounds, (ii) free radical inhibitors, and (iii) deuterium-containing reagents.

A still further aspect of the invention relates to a composition, comprising a precursor as described herein and a pre-reaction-combating agent for said precursor, said pre-reaction-combating agent being selected from the group consisting of (i) heteroatom (O, N, S) organo Lewis base compounds, (ii) free radical inhibitors, and (iii) deuterium-containing reagents.

In a further aspect, the invention relates to a method of combating pre-reaction of a vapor phase precursor described herein in contact with a substrate for deposition of a film component thereon. The method involves contacting said substrate, prior to said contact of the vapor phase precursor therewith, with a pre-reaction-combating agent selected from the group consisting of (i) heteroatom (O, N, S) organo Lewis base compounds, (ii) free radical inhibitors, and (iii) deuterium-containing reagents.

In a further aspect, the invention relates to a process wherein the pre-reaction combating reagent is introduced to passivate the surface of a growing film or slow the deposition rate, followed by reactivation using an alternative precursor or co-reactant (for example $H_2$, $NH_3$, plasma, $H_2O$, hydrogen sulfide, hydrogen selenide, diorganotellurides, diorganosulfides, diorganoselenides, etc.). Such passivation/retardation followed by reactivation thus may be carried out in an alternating repetitive sequence, for as many repetitive cycles as desired, in ALD or ALD-like processes. Pre-reaction-combating agents can be selected from the group consisting of (i) heteroatom (O, N, S) organo Lewis base compounds, (ii) free radical inhibitors, and (iii) deuterium-containing reagents.

Another aspect of the invention relates to a vapor phase deposition process for forming a film on a substrate involving cyclic contacting of the substrate with at least one film precursor described herein that is undesirably pre-reactive in the vapor phase. The process involves introducing to said film during growth thereof a pre-reaction-combating reagent that is effective to passivate a surface of said film or to slow rate of deposition of said film precursor, and after introducing said pre-reaction-combating reagent, reactivating said film with a different film precursor.

Other aspects, features and embodiments of the invention will be more fully apparent from the ensuing disclosure and appended claims.

DETAILED DESCRIPTION

Figure 1:
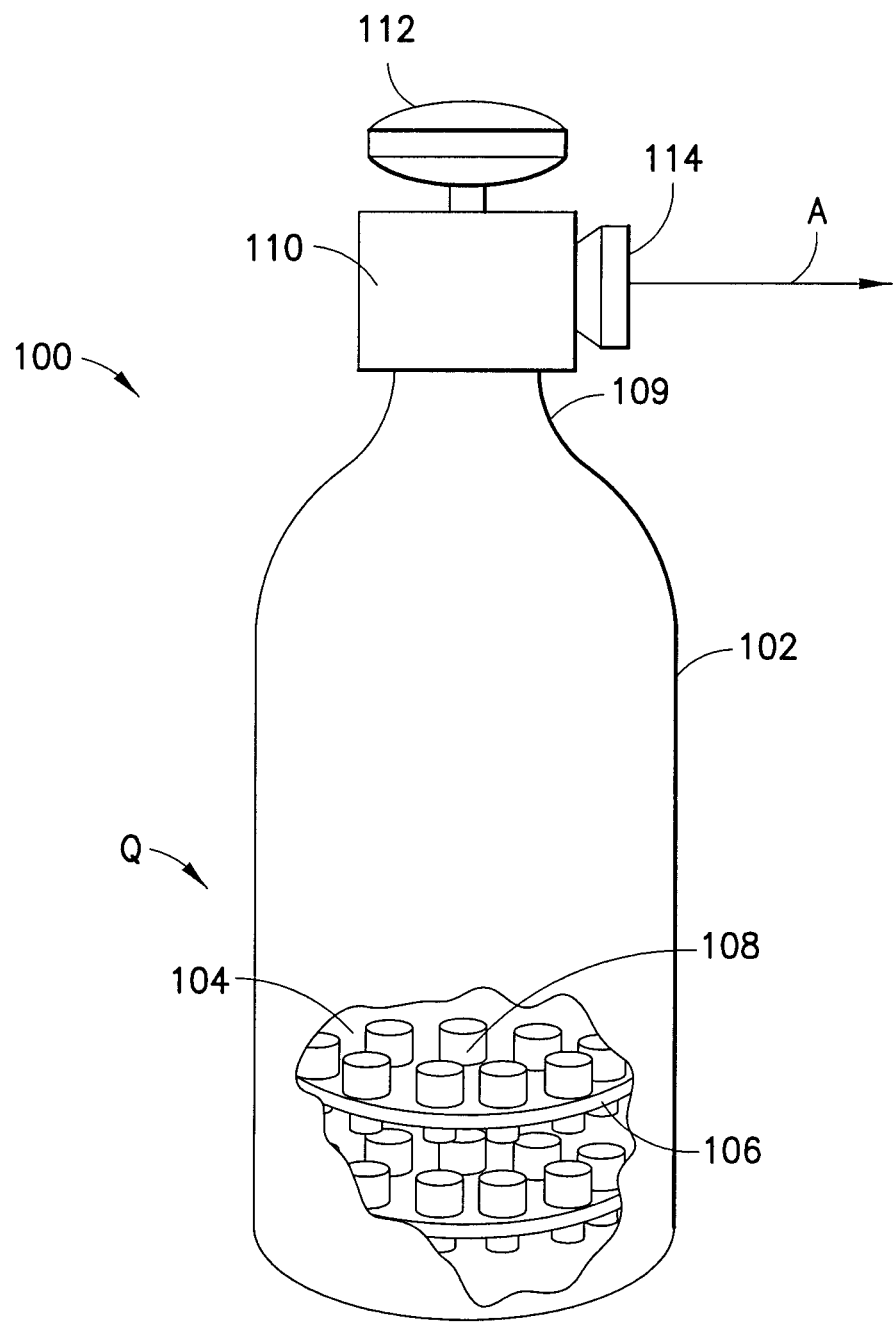
FIG. 1 is a schematic representation of a material storage and dispensing package containing a precursor of the present invention, in one embodiment thereof.
Figure 2:
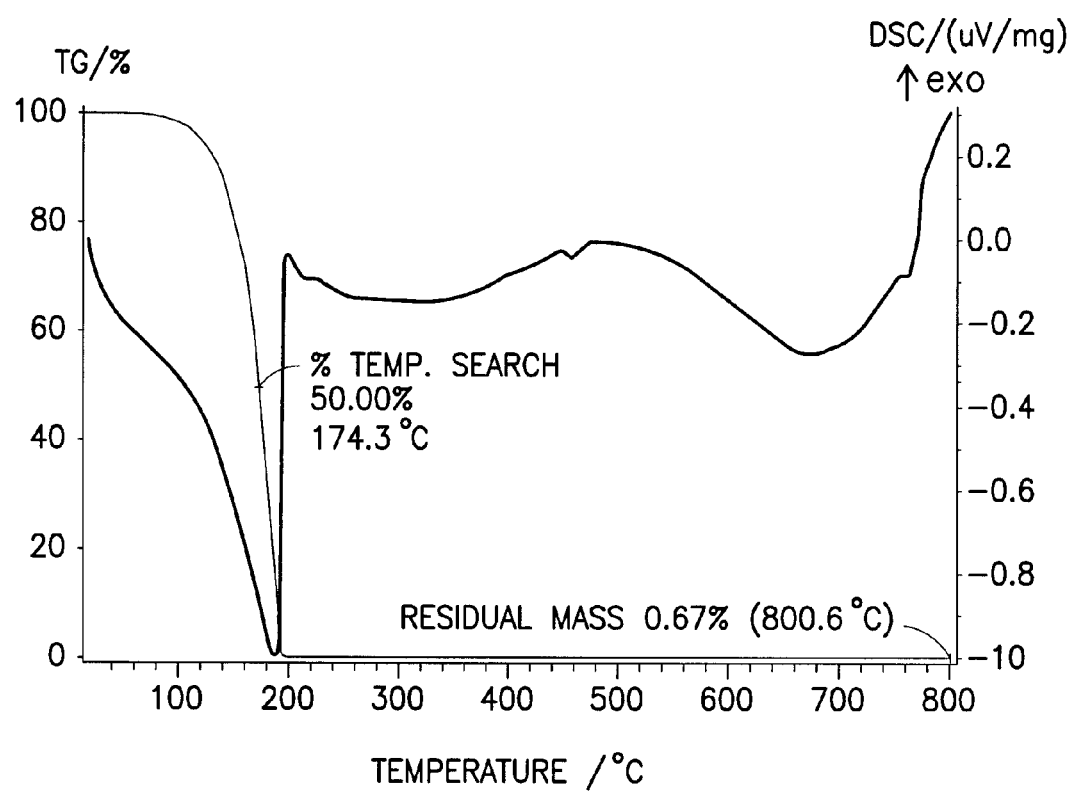
FIG. 2 is a STA plot of a typical Sb precursor, {tBuNCH$_2$CH$_2$NtBu}SbNMe$_2$.
Figure 3:
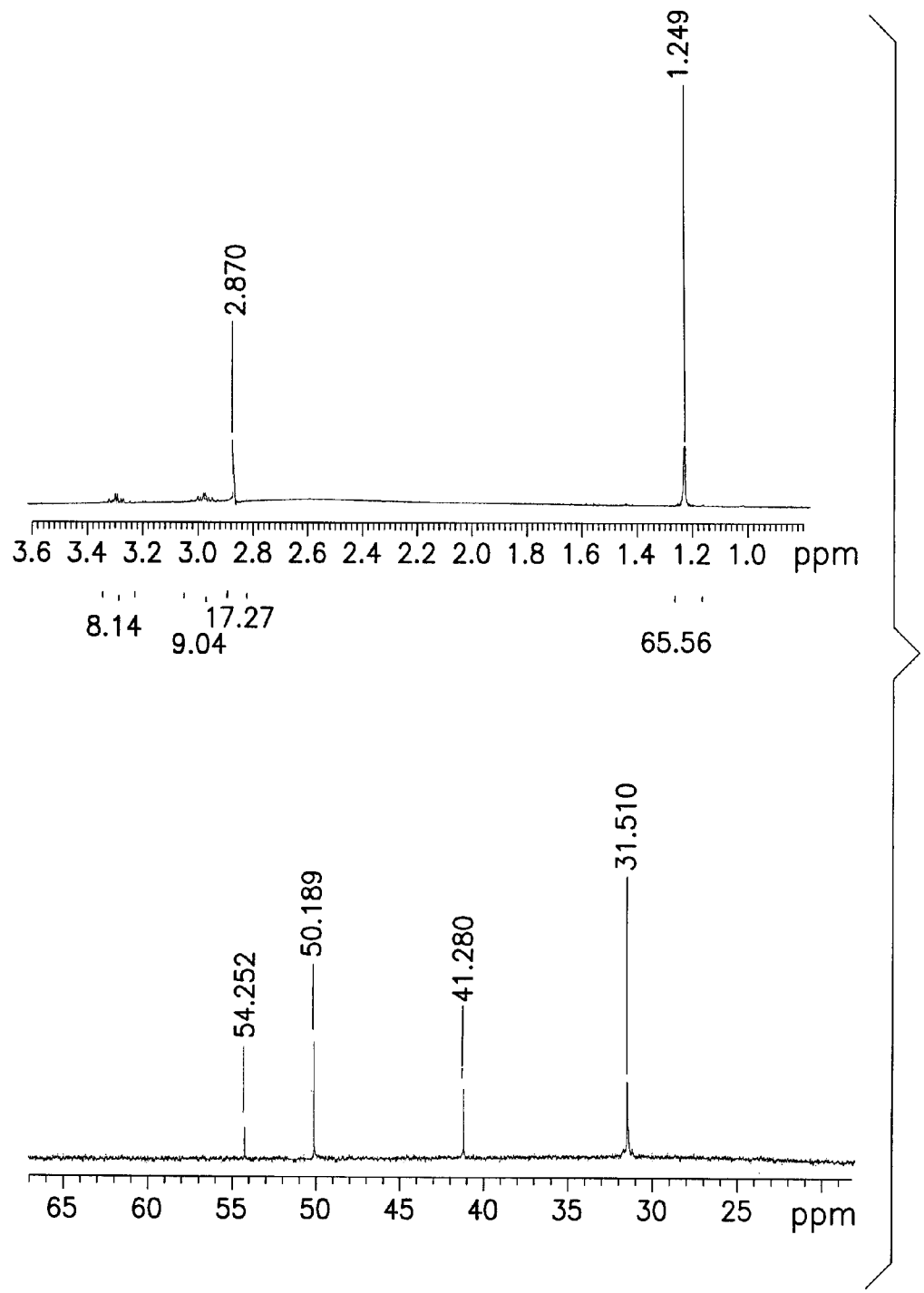
FIG. 3 shows $^1$H and $^{13}$NMR spectra for {tBuNCH$_2$CH$_2$NtBu}SbNMe$_2$.

The present invention relates to antimony precursors useful in film-forming applications, e.g., in chemical vapor deposition and atomic layer deposition applications, to form corresponding antimony-containing films on substrates, as well as associated processes of making and using such precursors, and packaged forms of such precursors.

As used herein, the term "film" refers to a layer of deposited material having a thickness below 1000 micrometers, e.g., from such value down to atomic monolayer thickness values. In various embodiments, film thicknesses of deposited material layers in the practice of the invention may for example be below 100, 10, or 1 micrometers, or in various thin film regimes below 200, 100, or 50 nanometers, depending on the specific application involved. As used herein, the term "thin film" means a layer of a material having a thickness below 1 micrometer. In addition, "thin film" refers to material deposited into high-aspect ratio narrow trench and via structures <90 nm.

As used herein, the singular forms "a", "and", and "the" include plural referents unless the context clearly dictates otherwise.

As used herein, the identification of a carbon number range, e.g., in $C_1$-$C_{12}$ alkyl, is intended to include each of the component carbon number moieties within such range, so that each intervening carbon number and any other stated or intervening carbon number value in that stated range, is encompassed, it being further understood that sub-ranges of carbon number within specified carbon number ranges may independently be included in smaller carbon number ranges, within the scope of the invention, and that ranges of carbon numbers specifically excluding a carbon number or numbers are included in the invention, and sub-ranges excluding either or both of carbon number limits of specified ranges are also included in the invention. Accordingly, $C_1$-$C_{12}$ alkyl is intended to include methyl, ethyl, propyl, butyl, pentyl, hexyl, heptyl, octyl, nonyl, decyl, undecyl and dodecyl, including straight chain as well as branched groups of such types. It therefore is to be appreciated that identification of a carbon number range, e.g., $C_1$-$C_{12}$, as broadly applicable to a substituent moiety, enables, in specific embodiments of the invention, the carbon number range to be further restricted, as a sub-group of moieties having a carbon number range within the broader specification of the substituent moiety. By way of example, the carbon number range $C_1$-$C_{12}$ alkyl, may be more restrictively specified, in particular embodiments of the invention, to encompass sub-ranges such as $C_1$-$C_4$ alkyl, $C_2$-$C_8$ alkyl, $C_2$-$C_4$ alkyl, $C_3$-$C_5$ alkyl, or any other sub-range within the broad carbon number range.

The precursors of the invention may be further specified in specific embodiments by provisos or limitations excluding specific substituents, groups, moieties or structures, in relation to various specifications and exemplifications thereof set forth herein. Thus, the invention contemplates restrictively defined compositions, e.g., a composition wherein $R^i$ is $C_1$-$C_{12}$ alkyl, with the proviso that $R^i \neq C_4$ alkyl when $R^j$ is silyl.

The invention relates in one aspect to antimony-containing precursors useful for low temperature (T<400° C.) deposition of Sb-containing films, e.g., for forming germanium-antimony-antimony (GST) films such as $Ge_2Sb_2Te_5$ on substrates such as wafers in the production of phase change random access memory devices.

The antimony-containing precursors described herein are suitable for forming such films by techniques such as atomic layer deposition (ALD) and chemical vapor deposition (CVD). Preferred precursors of such type have high volatility and desirable transport properties for ALD and CVD applications.

In accordance with another aspect of the invention, the antimony-containing precursors described herein are used to form Sb-containing highly conformal films of superior character by a vapor deposition process such as ALD or CVD.

The antimony-containing precursors described herein as being useful for the aforementioned film-forming applications can readily be formed by the following generalized reaction:

General Procedure for Synthesizing the Antimony Compounds:

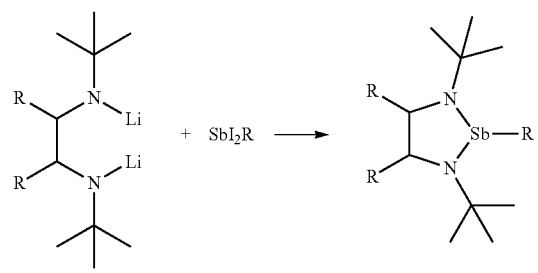

wherein each R is the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl, amidinate —C(NR$_2$)(NR$_3$)R$_4$, guanidinate —C(NR$_2$)(NR$_3$)NR$^4$R$^5$, isourate, cyclopendienyl ($C_5R_5$), guanidinate (—N=C—(NMe$_2$)$_2$), When preparing the compounds, it alternatively may be advantageous to start with an antimony trihalide, then form the ring as described above, leaving a single halogen on the antimony. This halogen can be reacted with an anionic reagent such as lithium-cyclopentadienide compound to form the desired products. This reaction scheme is outlined below:

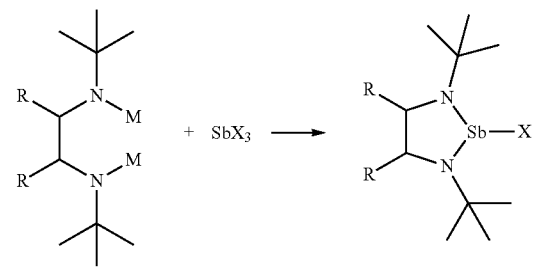

wherein

M=Li, Na, or K;

X=Cl, Br, or I;

each of $R^1$, $R^2$, $R^3$ and $R^4$ is the same as or different from others, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl.

Another synthetic approach is to react the neutral diamine directly with an antimony trihalide in the presence of a base to scavenge the liberated HCl according to the scheme below:

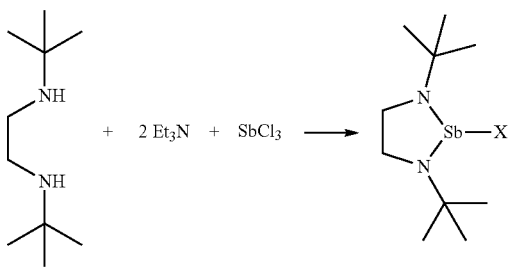

Then, the resulting compound can be reacted with a cyclopentadienyl anion to form compounds of the formula:

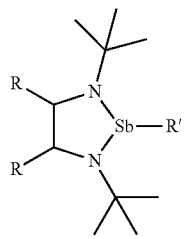

wherein the R' group attached to the antimony atom is a cyclopentadienyl moiety, as shown below:

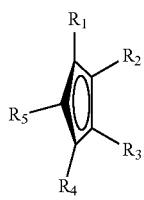

The antimony-containing precursors described herein are usefully employed as CVD/ALD precursors for the deposition of Sb-containing films, e.g., by liquid delivery techniques in which such compounds are provided in compositions including suitable solvent media. Useful solvents for such purpose in specific applications may include, without limitation, alkanes (e.g., hexane, heptane, octane, and pentane), aromatics (e.g., benzene or toluene), and amines (e.g., triethylamine, tert-butylamine). The solvent medium in which the Sb precursor or precursors are dissolved or suspended may be a single-component solvent or a multi-component solvent composition.

The precursors when in a liquid state can also be delivered neat using ALD/CVD liquid delivery techniques, in which the liquid is volatilized to form a corresponding precursor vapor, which then is contacted with the substrate on which the antimony-containing film is to be formed, under appropriate vapor deposition conditions.

When the precursors are in a solid state, they may be volatilized for delivery using any suitable solid delivery system, such as the solid delivery and vaporizer unit commercially available under the trademark ProE-Vap from ATMI, Inc. (Danbury, Conn., USA). The precursor or precursors (since the invention contemplates use of multiple Te precursors of differing type) are volatilized to form the corresponding precursor vapor which then is contacted with a wafer or other substrate to deposit an antimony-containing layer thereon.

The precursor vapor formed from the Sb precursor may be mixed with carrier or co-reactant gases in various embodiments, to obtain desired deposition thicknesses, growth rates, etc., as will be apparent to those skilled in the art.

The invention in a further aspect relates to a novel synthetic route for the preparation of bridging diamide antimony compounds. The new synthesis technique overcomes the difficulties and complexity of prior art synthetic approaches, as variously involving low yields and generation of side products that restricts recovery of high purity products, and forms monomeric complexes through chelation rather than bridging multiple metal centers resulting in higher nuclearity complexes including dimeric, oligomeric, and polymeric structures. In a specific aspect, the invention provides antimony bis-amides that are useful for low temperature deposition of antimony amides on substrates.

The antimony-containing precursors have been, at least in some cases, characterized by NMR spectroscopy and thermal analysis (TGA/DSC), as low melting solids which show good transport properties and low residual mass (<5%). Thus, the compounds are usefully employed as a precursor for the low temperature deposition of antimony-containing films.

The invention therefore provides a number of antimony-containing compounds of a useful character for ALD or CVD deposition of antimony or antimony-containing films, e.g., for fabricating GST devices comprising $Ge_2Sb_2Te_5$ films.

The following reaction scheme therefore may be used for production of such antimony precursors.

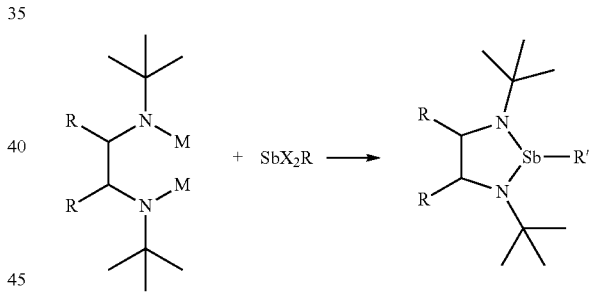

wherein

X is halogen,

M is Li, Na, or K, and each R is, independently, the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl, amidinate —C(NR$_2$)(NR$_3$)R$_4$, guanidinate —C(NR$_2$)(NR$_3$)NR$^4$R$^5$, isourate, cyclopendienyl ($C_5R_5$), guanidinate (—N=C—(NMe$_2$)$_2$), When preparing the compounds, it alternatively may be advantageous to start with an antimony trihalide, then form the ring as described above, leaving a single halogen on the antimony. This halogen can be reacted with an anionic reagent such as lithium-cyclopentadienide compound to form the desired products. This reaction scheme is outlined below:

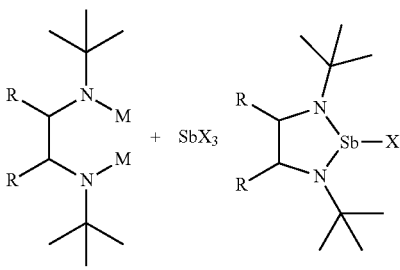

wherein
M=Li, Na, or K;
X=Cl, Br, or I;
each of $R^1$, $R^2$, $R^3$ and $R^4$ is the same as or different from others, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl.

Another synthetic approach is to react the neutral diamine directly with an antimony trihalide in the presence of a base to scavenge the liberated HCl according to the scheme below:

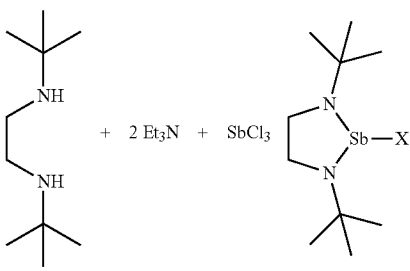

Then, the resulting compound can be reacted with a cyclopentadienyl anion to form compounds of the formula:

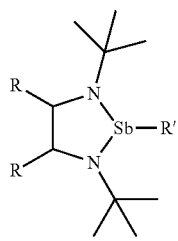

wherein the R' group attached to the antimony atom is a cyclopentadienyl moiety, as shown below:

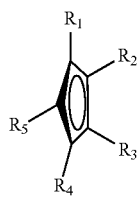

Where $R_{1-4}$ are as described above, and wherein the attachment to the Sb can result in either σ- or π-bonded complexes as illustrated by the following specific compounds:

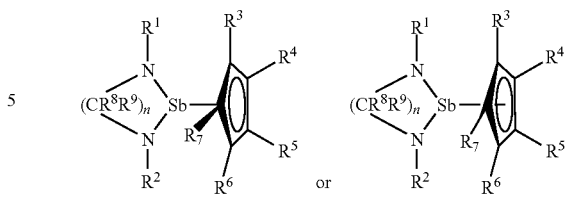

Alternatively, a similar synthesis can be performed, in which the starting diamines have a different chain length, to produce cyclic diamido-antimony compounds of a different size than a five-membered ring using a similar strategy as described above.

The following reaction scheme therefore may be used for production of such antimony precursors.

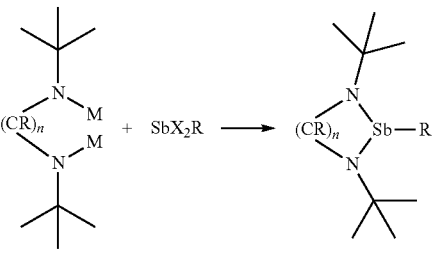

wherein
M=Li, Na, or K;
X=Cl, Br, or I;
and n is an integer between 1 and 6
each R is the same as or different from others, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl, acetylalkyl, and optionally-substituted cyclopentadienyl.

The same variation in the reaction can be used in the embodiment used to specifically form the cyclopentadienyl analogue, where an optionally-substituted cyclopentadienyl anion is attached to the Sb atom.

The antimony-containing compounds described herein have high volatility and low decomposition temperatures, and thus are well suited for ALD and CVD applications.

These precursors accommodate low temperature deposition applications, having good volatilization and transport properties. They can be delivered in a neat form in the case of precursor compounds in liquid form, or in compositions including suitable solvent media. Useful solvents for such purpose in specific applications may include, without limitation, alkanes (e.g., hexane, heptane, octane, and pentane), aromatics (e.g., benzene or toluene), and amines (e.g., triethylamine, tert-butylamine) or mixtures thereof, as above described.

The precursors when in a solid state can be volatilized for delivery using any suitable solid delivery system, such as the solid delivery and vaporizer unit commercially available under the trademark ProE-Vap from ATMI, Inc. (Danbury, Conn., USA). The precursor or precursors (since the invention contemplates use of multiple Te precursors of differing type) are volatilized to form the corresponding precursor vapor which then is contacted with a wafer or other substrate to deposit an antimony-containing layer thereon, e.g., for forming a GST layer.

The invention in yet another aspect relates to antimony compounds with nitrogen donor ligands useful for deposition applications to deposit antimony or antimony-containing films on substrates, for applications such as GST phase change random access memory (PRAM) devices.

This aspect of the invention relates more specifically to Sb(III) precursors having at least one nitrogen-based ligand as described herein.

The antimony-containing precursors described herein can be used in film formation processes with appropriate co-reactants, e.g., in a continuous deposition mode (CVD) or pulsed/atomic layer deposition mode (ALD), to deposit films of superior character.

For metal-like films, reducing atmospheres are advantageously used. The precursors of the invention can be utilized as low temperature deposition precursors with reducing co-reactants such as hydrogen, $H_2$/plasma, amines, imines, hydrazines, silanes, germanes such as $GeH_4$, ammonia, alkanes, alkenes and alkynes. For CVD modes of film formation, reducing agents such as $H_2$, and $NH_3$ are preferred, and plasmas of these co-reactants may be used in digital or ALD mode, wherein the co-reactants are separated from the precursor in a pulse train, utilizing general CVD and ALD techniques within the skill of the art, based on the disclosure herein. More aggressive reducing agents can also be used in a digital or ALD mode since co-reactants can be separated, preventing gas phase reactions. For ALD and conformal coverage in high aspect ratio structures, the precursor preferably exhibits self-limiting behavior in one type of atmosphere (e.g., inert or weakly reducing/oxidizing gas environments) and exhibits rapid decomposition to form a desired film in another type of atmosphere (e.g., plasma, strongly reducing/oxidizing environments).

Formation of Chalcogenide Films with Pre-Reaction-Combating Agents

The invention in another aspect involves use of control agents to combat vapor phase pre-reaction of the precursors described herein, that otherwise causes uneven nucleation on the substrate, longer incubation times for deposition reactions, and lower quality product films. Such pre-reaction may for example be particularly problematic in applications involving chalcogenide films, related source materials (O, S, Se, Te, Ge, Sb, Bi, etc.), and/or manufacture of phase change memory and thermoelectric devices.

Pre-reaction may occur when the precursor reagents described herein are introduced to the deposition chamber, as in chemical vapor deposition, and may also occur in atomic layer deposition (ALD) processes, depending on the specific arrangement of ALD cycle steps and the specific reagents involved.

The invention therefore contemplates the use of control agents with the precursors described herein, whereby detrimental gas phase pre-reactions are suppressed, mitigated or eliminated, so that deposition reactions are induced/enhanced on the substrate surface, and films of superior character are efficiently formed.

The control agents that can be utilized with precursors of the invention for such purpose include agents selected from the group consisting of (i) heteroatom (O, N, S) organo Lewis base compounds, (ii) free radical inhibitors, and (iii) deuterium-containing reagents.

These agents can be utilized to lessen deleterious gas phase pre-reaction I'll precursors by various approaches, including:
(1) addition to the precursor composition of a pre-reaction suppressant comprising one or more heteroatom (O, N, S) organo Lewis base compounds such as 1,4-dioxane, thioxane, ethers, polyethers, triethylamine (TEA), triazine, diamines, N,N,N',N'-tetramethylethylenediamine, N,N,N'-trimethylethylenediamine, amines, imines, and pyridine;
(2) addition to the precursor composition of a free radical inhibitor, such as butylated hydroxy toluene (BHT), hydroquinone, butylated hydro anisole (BHA), diphenylamine, ethyl vanillin, etc.;
(3) use of modified chalcogenide precursors, in which hydrogen substituents have been replaced with deuterium (D) substituents, to provide deuterated analogs for vapor phase deposition; and
(4) addition to the precursor composition of a deuterium source, to deuterate the precursor in situ.

The pre-reaction-combating agents described above (suppressants, free radical inhibitors, deuterium sources and/or deuterated precursors) can be introduced to any of the feed streams to the vapor deposition process in which the film is to be formed. For example, such pre-reaction-combating agents can be introduced to one or more of precursor feed stream(s), inert carrier gas stream(s) to which chalcogenide precursor(s) or other reagents are subsequently added for flow to the deposition chamber, co-reactant feed stream(s) flowed to the deposition chamber, and/or any other stream(s) that is/are flowed to the deposition chamber and in which the pre-reaction-combating agent(s) is/are useful for reduction or elimination of premature reaction of the precursors that would otherwise occur in the absence of such agent(s).

The aforementioned suppressants, free radical inhibitors and/or deuterium source reagents in specific embodiments are co-injected with the precursor(s), e.g., metal source reagent(s), to effect at least partial reduction of pre-reaction involving the precursor(s) and reagent(s).

The pre-reaction-combating agent can alternatively be added directed to the deposition locus, e.g., the deposition chamber to which the precursor vapor is introduced for contacting with the substrate to deposit the film thereon, to suppress deleterious vapor phase pre-reaction involving the precursor(s) and/or other reagents.

As another approach, in the broad practice of the present invention, the suppressant, free radical inhibitor and/or deuterium source can be added to a solution containing the precursor and/or another metal source reagent, and the resulting solution can be utilized for liquid delivery processing, in which the solution is flowed to a vaporizer to form a source vapor for contacting with the substrate to deposit the deposition species thereon.

Alternatively, if the precursor and/or another metal source reagent are not in an existing solution, the suppressant, free radical inhibitor and/or deuterium source can be added to form a mixture or a solution with the precursor and/or another metal source reagent, depending on the respective phases of the materials involved, and their compatibility/solubility.

As a still further approach, the suppressant, free radical inhibitor and/or deuterium source can be utilized for surface treatment of the substrate prior to contacting of the substrate with the precursor and/or other metal source reagent.

The invention therefore contemplates various vapor deposition compositions and processes for forming films on substrates, in which pre-reaction of the precursors is at least partially attenuated by one or more pre-reaction-combating agents selected from among heteroatom (O, N, S) organo Lewis base compounds, sometimes herein referred to as suppressor agents, free radical inhibitors, and/or deuterium source reagents. Use of previously synthesized deuterated precursors or organometal compounds is also contemplated, as an alternative to in situ deuteration with a deuterium source. By suppressing precursor prereaction with these approaches, product films of superior character can be efficiently formed.

The control agent can be used for combating pre-reaction of chalcogenide precursor in a process in which multiple feed streams are flowed to a deposition locus to form a film on a substrate, wherein at least one of the multiple feed streams includes a precursor susceptible to pre-reaction adversely affecting the film, in which the method involves introducing the control agent to at least one of such multiple feed streams or supplied materials therefor, or to the deposition locus.

The pre-reaction combating reagent alternatively can be introduced to passivate the surface of a growing chalcogenide film or slow the deposition rate, followed by reactivation using an alternative precursor or co-reactant (for example $H_2$, $NH_3$, plasma, $H_2O$, hydrogen sulfide, hydrogen selenide, diorganotellurides, diorganosulfides, diorganoselenides, etc.), thereby carrying out passivation/retardation followed by reactivation steps, e.g., as an alternating repetitive sequence. Such sequence of passivation/retardation followed by reactivation can be carried out for as many repetitive cycles as desired, in ALD or ALD-like processes. The steps may be carried out for the entire deposition operation, or during some initial, intermediate or final portion thereof.

The invention therefore contemplates precursor compositions including the precursor and the pre-reaction-combating reagent. Within the categories of pre-reaction-combating reagents previously described, viz., (i) heteroatom (O, N, S) organo Lewis base compounds, (ii) free radical inhibitors, and (iii) deuterium-containing reagents, suitable pre-reaction-combating reagents for specific applications may be readily determined within the skill of the art, based on the disclosure herein.

Heteroatom (O, N, S) organo Lewis base compounds may be of varied type, e.g., containing an oxo (—O—) moiety, a nitrogen ring atom or pendant amino or amide substituent, a sulfur ring atom or pendant sulfide, sulfonate or thio group, as effective to at least partially lessen pre-reaction of the precursor and other organo metal reagents in the process system. Illustrative examples of heteroatom (O, N, S) organo Lewis base compounds having utility in specific applications of the invention include, without limitation, 1,4-dioxane, thioxane, ethers, polyethers, triethylamine, triazine, diamines, N,N,N', N'-tetramethylethylenediamine, N,N,N'-trimethylethylenediamine, amines, imines, pyridine, and the like.

The heteroatom organo Lewis base compound in various specific embodiments of the invention may include a guanidinate compound, e.g., $(Me_2N)_2C=NH$.

One preferred class of heteroatom organo Lewis base compounds for such purpose includes $R_3N$, $R_2NH$, $RNH_2$, $R_2N(CH_2)_xNR_2$, $R_2NH(CH_2)_xNR_2$, $R_2N(CR_2)_xNR_2$, and cyclic amines —$N(CH_2)_x$—, imidazole, thiophene, pyrrole, thiazole, urea, oxazine, pyran, furan, indole, triazole, triazine, thiazoline, oxazole, dithiane, trithiane, crown ethers, 1,4,7-triazacyclononane, 1,5,9-triazacyclododecane, cyclen, succinamide, and substituted derivatives of the foregoing, wherein R can be hydrogen or any suitable organo moieties, e.g., hydrogen, $C_1$-$C_8$ alkyl, $C_1$-$C_8$ alkoxy, $C_1$-$C_8$ alkene, $C_1$-$C_8$ alkyne, and $C_1$-$C_8$ carboxyl, and wherein x is an integer having a value of from 1 to 6.

The heteroatom organo Lewis base compounds may be utilized in the precursor composition at any suitable concentration, as may be empirically determined by successive deposition runs in which the heteroatom organo Lewis base compound concentration is varied, and character of the resulting film is assessed, to determine an appropriate concentration. In various embodiments, the heteroatom organo Lewis base compound may be utilized in the concentration of 1-300% of the amount of precursor. Specific sub-ranges of concentration values within a range of 0.01-3 equivalents of the heteroatom organo Lewis base compound may be established for specific classes of precursors, without undue experimentation, based on the disclosure herein.

The pre-reaction-combating reagent may additionally or alternatively comprise free radical inhibitors that are effective to lessen the extent of pre-reaction between the precursor and another organo metal reagent. Such free radical inhibitors may be of any suitable type, and may for example include hindered phenols. Illustrative free radical inhibitors include, without limitation, free radical scavengers selected from the group consisting of: 2,6-ditert-butyl-4-methyl phenol, 2,2,6,6-tetramethyl-1-piperidinyloxy, 2,6-dimethylphenol, 2-tert-butyl-4-hydroxyanisole, 3-tert-butyl-4-hydroxyanisole, propyl ester 3,4,5-trihydroxy-benzoic acid, 2-(1,1-dimethylethyl)-1,4 benzenediol, diphenylpicrylhydrazyl, 4-tert-butylcatechol, N-methylaniline, 2,6-dimethylaniline, p-methoxydiphenylamine, diphenylamine, N,N'-diphenyl-p-phenylenediamine, p-hydroxydiphenylamine, phenol, octadecyl-3-(3,5-di-tert-butyl-4-hydroxyphenyl)propionate, tetrakis(methylene (3,5-di-tert-butyl-4-hydroxy-hydrocinnamate) methane, phenothiazines, alkylamidonoisoureas, thiodiethylene bis(3,5,-di-tert-butyl-4-hydroxy-hydrocinnamate, 1,2,-bis(3,5-di-tert-butyl-4-hydroxyhydrocinnamoyl)hydrazine, tris(2-methyl-4-hydroxy-5-tert-butylphenyl)butane, cyclic neopentanetetrayl bis (octadecyl phosphite), 4,4'-thiobis(6-tert-butyl-m-cresol, 2,2'-methylenebis(6-tert-butyl-p-cresol), oxalyl bis(benzylidenehydrazide) and mixtures thereof. Preferred free radical inhibitors include BHT, BHA, diphenylamine, ethyl vanillin, and the like.

Useful concentrations of the free radical inhibitor may be in a range of from 0.001 to about 0.10% by weight of the weight of the precursor, in various specific embodiments. More generally, any suitable amount of free radical inhibitor may be employed that is effective to combat the pre-reaction of the precursor in the delivery and deposition operations involved in the film formation process.

The deuterium source compounds afford another approach to suppressing pre-reaction of the chalcogenide precursor. Such deuterium source compounds may be of any suitable type, and may for example include deuterated pyridine, deuterated pyrimidine, deuterated indole, deuterated imidazole, deuterated amine and amide compounds, deuterated alkyl reagents, etc., as well as deuterated analogs of the precursors that would otherwise be used as containing hydrogen or protonic substituents.

Deuterides that may be useful in the general practice of invention as pre-reaction-combating reagents include, without limitation, germanium and antimony compounds of the formulae $R_xGeD_{4-x}$ and $R_xSbD_{3-x}$ wherein R can be hydrogen or any suitable organo moieties, e.g., hydrogen, $C_1$-$C_8$ alkyl, $C_1$-$C_8$ alkoxy, $C_1$-$C_8$ alkene, $C_1$-$C_8$ alkyne, and $C_1$-$C_8$ carboxyl, and wherein x is an integer having a value of from 1 to 6.

The deuterium source reagent may be utilized at any suitable concentration that is effective to combat pre-reaction of the precursor. Illustrative deuterium source reagent concentrations in specific embodiments of the invention can be in a range of 0.01 to about 5% by weight, based on the weight of precursor.

Thus, a deuterium source compound may be added to one or more of the feed streams to the vapor deposition process, and/or one of the precursors or other feed stream components may be deuterated in the first instance.

The concentrations of the pre-reaction-combating agents utilized in the practice of the present invention to at least partially eliminate pre-reaction of the precursors can be widely varied in the general practice of the present invention, depending on the temperatures, pressures, flow rates and specific compositions involved. The above-described ranges of concentration of the pre-reaction-combating reagents of the invention therefore are to be appreciated as being of an illustrative character only, with applicable concentrations being readily determinable within the skill of the art, based on the disclosure herein.

The specific mode of introduction or addition of the pre-reaction-combating agent to one or more of the feed streams to the deposition process may correspondingly be varied, and may for example employ mass flow controllers, flow control valves, metering injectors, or other flow control or modulating components in the flow circuitry joining the source of the pre-reaction-combating agent with the streams being flowed to the deposition process during normal film-forming operation. The process system may additionally include analyzers, monitors, controllers, instrumentation, etc., as may be necessary or appropriate to a given implementation of the invention.

In lieu of introduction or addition of the pre-reaction-combating agent to one or more of the flow streams to the vapor deposition process, the pre-reaction-combating agent may be mixed with precursor in the first instance, as a starting reagent material for the process. For example, the pre-reaction-combating agent may be mixed in liquid solution with the precursor, for liquid delivery of the resulting precursor solution to a vaporizer employed to generate precursor vapor for contact with the substrate to deposit the film thereon.

As mentioned, the pre-reaction-combating agent may be added to the deposition locus to provide active gas-phase suppression of pre-reaction of the precursor vapor(s) that would otherwise be susceptible to such deleterious interaction.

As a still further alternative, the pre-reaction-combating agent may be used as a preliminary surface treatment following which the precursor and co-reactants (e.g., $H_2$, $NH_3$, plasma, $H_2O$, hydrogen sulfide, hydrogen selenide, diorganotellurides, diorganosulfides, diorganoselenides, etc.) are delivered to the substrate surface to effect deposition on such surface. For such purpose, the pre-reaction-combating agent may be introduced into one or more of the flow lines to the deposition process and flow to the substrate in the deposition process chamber, prior to initiation of flow of any precursors. After the requisite period of contacting of the substrate with such pre-reaction-combating agent has been completed, the flow of the pre-reaction-combating agent can be terminated, and normal feeding of flow streams to the deposition chamber can be initiated.

It will be apparent from the foregoing description that the pre-reaction-combating agent may be introduced in any of a wide variety of ways to effect diminution of the pre-reaction of the precursor in the deposition system.

In one embodiment of the invention, a vapor phase deposition system is contemplated, comprising:

a vapor deposition chamber adapted to hold at least one substrate for deposition of a film thereon;

chemical reagent supply vessels containing reagents for forming the film;

first flow circuitry arranged to deliver said reagents from said chemical reagent supply vessels to the vapor deposition chamber;

a pre-reaction-combating agent supply vessel containing a pre-reaction-combating agent;

second flow circuitry arranged to deliver the pre-reaction-combating agent from the pre-reaction-combating agent supply vessel to the first flow circuitry, to said chemical reagent supply vessels and/or to the vapor deposition chamber.

Figure 4:
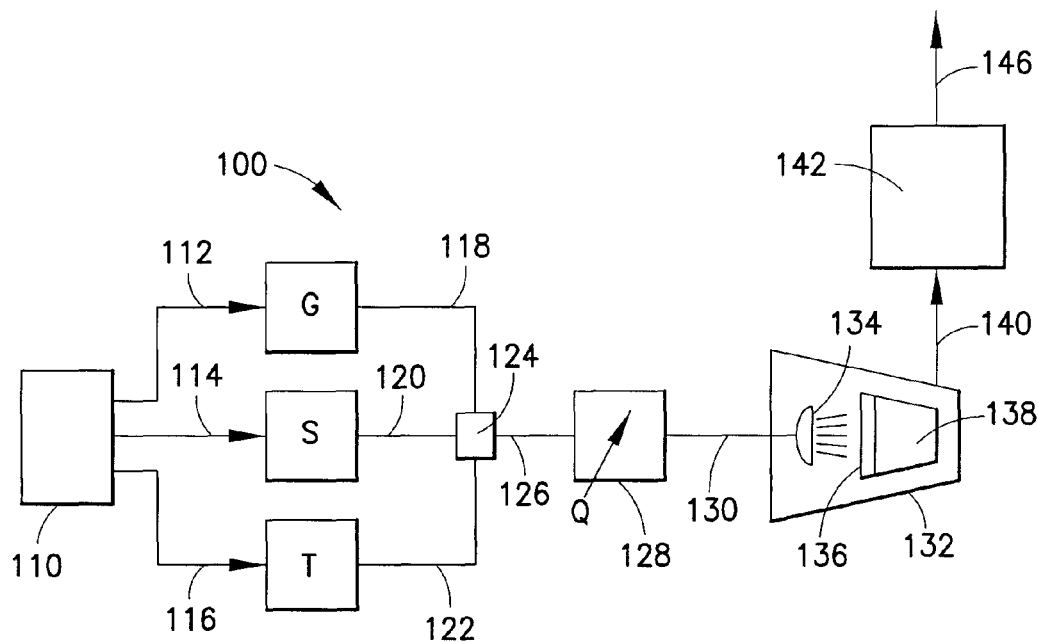
FIG. 4 is a schematic representation of a vapor deposition system according to one embodiment of the present invention, wherein suppression of pre-reaction of the precursors is achieved by addition of pre-reaction-combating reagent to one or more feed streams in the vapor deposition system.

Referring now to the drawings, FIG. 4 is a schematic representation of a vapor deposition system 100 in one embodiment thereof.

In this illustrative system, a pre-reaction-combating agent is contained in a supply vessel 110. The pre-reaction-combating agent can comprise a pre-reaction suppressant, a free radical inhibitor, a deuterium source, or a combination of two or more such agents and/or types of such agents.

The pre-reaction-combating agent supply vessel is joined by respective flow lines 112, 114 and 116, to germanium, antimony and tellurium reagent supply vessels, labeled "G," "S" and "T," respectively. The germanium precursor in vessel "G" may be a tetraalkyl or tetraamido germanium compound, such as tetramethyl germanium, tetraethyl germanium, tetraallyl germanium, tetrakis(dimethylamino)germane or other organo germanium compounds. Furthermore, precursor "G" may be a germylene compound wherein the lone pair on Ge(II) can react in the gas-phase with chalcogen precursors in the absence of a pre-reaction suppressant. The antimony precursor in vessel "S" can be a trialkyl or triamido antimony compound, such as tributyl antimony, triisopropyl antimony, tris(dimethylamino)antimony or other organo antimony compound. The tellurium precursor in vessel "T" can be a dialkyl or diamido tellurium compound, such as diisopropyl tellurium, dibutyl tellurium, bis[bis(trimethylsilyl)-amino]tellurium or other organo tellurium compound.

The pre-reaction-combating agent therefore can be added to any of the germanium, antimony and/or tellurium precursors in the respective "G," "S" and "T" vessels, via the corresponding flow line(s), which for such purpose may have flow control valves or other flow-modulating components therein.

In the specific process embodiment shown, the germanium, antimony and tellurium precursors are flowed in liquid form in feed lines 118, 120 and 122, respectively, to the mixing chamber 124, and the resulting precursor mixture then is flowed from the mixing chamber 124 in line 126 to vaporizer 128. In the vaporizer, the liquid precursor mixture and pre-reaction-combating agent are volatilized to form a precursor vapor. The precursor vapor then flows in line 130 to the showerhead disperser 134 in vapor deposition chamber 132, for discharge of precursor mixture onto the wafer substrate 136 mounted on susceptor 138 in the deposition chamber.

The precursor vapor contacting the wafer substrate 136 serves to deposit the germanium, antimony and tellurium metals on the substrate, to form a thin film of germanium-antimony-tellurium (GST) material, e.g., for manufacture of a phase change random access memory device.

The contacted precursor vapor, depleted in metals content, is discharged from the vapor deposition chamber 132 in line 140, and flows to the effluent abatement unit 142. In the effluent abatement unit 142, the discharged effluent vapor is treated, e.g., by scrubbing, catalytic oxidation, electrochemical treatment, or in other manner, to yield a final effluent that is discharged from the abatement unit in line 146.

It will be appreciated that these schematic representation of the vapor deposition system shown in FIG. 4 is of an illustrative character, and that numerous other arrangements could be utilized for deployment and use of the pre-reaction-combating agent, including those previously illustratively discussed herein. For example, the pre-reaction-combating agent could be introduced directly to the mixing chamber 124, for blending therein with the respective GST precursors.

Alternatively, the pre-reaction-combating agent could be introduced into manifold 118, or other mixing chamber, blender, etc., for combination with the precursor that is being transported to the deposition locus.

The system shown in FIG. 4 employs liquid delivery of the respective precursors. It will be recognized that if solid-phased precursors are employed, then solid delivery techniques may be employed, in which solid precursor is volatilized, e.g., by sublimation of the solid starting material.

In lieu of using a deuterating agent as the pre-reaction-combating agent in the FIG. 4 system, one or more of the germanium, antimony and tellurium precursors could be supplied in the first instance as a deuterated analog of an organo germanium, antimony or tellurium precursor, in which hydrogen substituents of the organo moiety have been replaced with deuterium.

The pre-reaction-combating reagents may be employed in the broad practice of the present invention to produce improved films for the manufacture of semiconductor products. In general, the pre-reaction-combating reagents described herein may be utilized in various combinations in specific applications, to suppress or eliminate pre-reaction of the precursor and provide superior nucleation and final film properties.

Liquid Delivery Formulations

Liquid delivery formulations can be employed in which precursors that are liquids may be used in neat liquid form, or liquid or solid precursors may be employed in suitable solvents, including for example alkane solvents (e.g., hexane, heptane, octane, and pentane), aryl solvents (e.g., benzene or toluene), amines (e.g., triethylamine, tert-butylamine), imines and hydrazines or mixtures thereof. The utility of specific solvent compositions for particular Te precursors may be readily empirically determined, to select an appropriate single component or multiple component solvent medium for the liquid delivery vaporization and transport of the specific antimony precursor that is employed. In the case of solid precursors of the invention, a solid delivery system may be utilized, for example, using the ProE-Vap solid delivery and vaporizer unit (commercially available from ATMI, Inc., Danbury, Conn., USA).

In general, the thicknesses of metal-containing layers formed using the precursors of the invention can be of any suitable value. In a specific embodiment of the invention, the thickness of the antimony-containing layer can be in a range of from 5 nm to 500 nm or more including both planar and trench/via geometries.

The various antimony precursor compounds of the invention can be utilized to form GST films in combination with any suitable germanium and antimony precursors, e.g., by CVD and ALD techniques, for applications such as PCRAM device manufacture. The process conditions useful for carrying out deposition of Sb-containing films can be readily determined within the skill of the art by the simple expedient of selectively varying the delivery and deposition process conditions and characterizing the resulting films, to determine the process conditions envelope most appropriate for a given deposition application.

In some embodiments, the antimony-containing films are formed on substrates, and can be, for example, GST films, amorphous SbTe films, or crystalline SbTe films, and can be applied, for example, using atomic layer deposition (ALD) or chemical vapor deposition (CVD) techniques. Such SbTe (e.g. $Sb_2Te_3$) films may also be employed in thermoelectric devices.

In another embodiment, amorphous SbTe can be produced by co-deposition of the antimony-containing compounds described herein, and antimony precursors such as di-t-butyl tellurium or diisopropyl tellurium, $Te(tBu)_2$ or $Te(iPr)_2$, at temperature in a range of from 250° C.-400° C., e.g., 320° C., using bubbler delivery of the antimony and tellurium-containing precursors in an inert carrier gas stream, e.g., $N_2$ at a flow rate of 20-50 sccm, e.g., 30 sccm. The respective tellurium and antimony precursors used for such deposition can be of any suitable types, and such precursors can be delivered for deposition at any suitable volumetric flow rate, e.g., for the aforementioned flow rate of 30 sccm for the illustrative antimony precursor, $Te(tBu)_2$, and the flow rate for the antimony-containing precursors can be on the order of 5 micromoles/minute. The resulting amorphous SbTe films will have an antimony content of approximately 20-70%.

FIG. 1 is a schematic representation of a material storage and dispensing package 100 containing an antimony precursor, according to one embodiment of the present invention.

The material storage and dispensing package 100 includes a vessel 102 that may for example be of generally cylindrical shape as illustrated, defining an interior volume 104 therein. In this specific embodiment, the precursor is a solid at ambient temperature conditions, and such precursor may be supported on surfaces of the trays 106 disposed in the interior volume 104 of the vessel, with the trays having flow passage conduits 108 associated therewith, for flow of vapor upwardly in the vessel to the valve head assembly for dispensing, in use of the vessel.

The solid precursor can be coated on interior surfaces in the interior volume of the vessel, e.g., on the surfaces of the trays 106 and conduits 108. Such coating may be effected by introduction of the precursor into the vessel in a vapor form from which the solid precursor is condensed in a film on the surfaces in the vessel. Alternatively, the precursor solid may be dissolved or suspended in a solvent medium and deposited on surfaces in the interior volume of the vessel by solvent evaporation. In yet another method the precursor may be melted and poured onto the surfaces in the interior volume of the vessel. For such purpose, the vessel may contain substrate articles or elements that provide additional surface area in the vessel for support of the precursor film thereon.

As a still further alternative, the solid precursor may be provided in granular or finely divided form, which is poured into the vessel to be retained on the top supporting surfaces of the respective trays 106 therein. As a further alternative, a metal foam body may be provided in the interior volume of the vessel, which contains porosity of a specific character adapted for retaining the solid particulate precursor for highly efficient vaporization thereof.

The vessel 102 has a neck portion 109 to which is joined the valve head assembly 110. The valve head assembly is equipped with a hand wheel 112 in the embodiment shown. In lieu of a hand wheel, the valve head assembly may in turn be coupled or operatively linked to a controller for automated operation. The valve head assembly 110 includes a dispensing port 114, which may be configured for coupling to a fitting or connection element to join flow circuitry to the vessel. Such flow circuitry is schematically represented by arrow A in FIG. 1, and the flow circuitry may be coupled to a downstream ALD or chemical vapor deposition chamber (not shown in FIG. 1).

In use, the vessel 102 can be heated with a suitable heater, such as a heating jacket, resistance heating elements affixed to the exterior wall surface of the vessel, etc., so that solid precursor in the vessel is at least partially volatilized to provide precursor vapor. The input of heat is schematically shown in FIG. 1 by the reference arrow Q. The precursor vapor is discharged from the vessel through the valve passages in the valve head assembly 110 when the hand wheel 112 or alternative valve actuator or controller is translated so that the valve is in an open position, whereupon vapor deriving from the precursor is dispensed into the flow circuitry schematically indicated by arrow A.

In lieu of solid delivery of the precursor, the precursor may be provided in a solvent medium, forming a solution or suspension. Such precursor-containing solvent composition then may be delivered by liquid delivery and flash vaporized to produce a precursor vapor. The precursor vapor is contacted with a substrate under deposition conditions, to deposit the metal on the substrate as a film thereon.

In one embodiment, the precursor is dissolved in an ionic liquid medium, from which precursor vapor is withdrawn from the ionic liquid solution under dispensing conditions.

As a still further alternative, the precursor may be stored in an adsorbed state on a suitable solid-phase physical adsorbent storage medium in the interior volume of the vessel. In use, the precursor vapor is dispensed from the vessel under dispensing conditions involving desorption of the adsorbed precursor from the solid-phase physical adsorbent storage medium.

Supply vessels for precursor delivery may be of widely varying type, and may employ vessels such as those commercially available from ATMI, Inc. (Danbury, Conn.) under the trademarks SDS, SAGE, VAC, VACSorb, and ProE-Vap, as may be appropriate in a given storage and dispensing application for a particular precursor of the invention.

The precursors of the invention thus may be employed to form precursor vapor for contacting with a substrate to deposit an antimony-containing thin film thereon.

In a preferred aspect, the invention utilizes the precursors to conduct atomic layer deposition, yielding ALD films of superior conformality that are uniformly coated on the substrate with high step coverage and conformality even on high aspect ratio structures.

Accordingly, the precursors of the present invention enable a wide variety of microelectronic devices, e.g., semiconductor products, flat panel displays, etc., to be fabricated with antimony-containing films of superior quality.

The present invention will be better understood with reference to the following non-limiting examples:

Example 1

Preparation of (tBuNCH$_2$CH$_2$NtBu)SbCl

General Procedures

All manipulations, unless otherwise noted, were performed under a dry nitrogen atmosphere with use of either a drybox or standard Schlenk techniques. Benzene-d$_6$ was dried over 4 Å molecular sieves. NMR spectra were recorded at 21° C. on a Mercury 300 MHz Fourier transform (FT) spectrometer and referenced to solvents (residual protons in the $^1$H spectra). n-BuLi in hexanes (1.6 M), and N,N'-diisopropylcarbodiimide were purchased from Aldrich and used as received. GeCl$_2$-dioxane was obtained from Gelest. THF, ether, and pentane were purchased from Aldrich and dried using a solvent drying system with activated alumina/molecular sieve columns before use.

A solution of N,N'-di-tert-butylethylenediamine (37.8 g, 47.2 mL, 219 mmol), triethylamine (44.4 g, 60.8 mL, 438 mmol) in diethylether (650 mL) was cooled in an ice-bath. A solution of antimony trichloride (50.0 g, 219 mmol) in ether (100 mL) was slowly added forming a thick white precipitate. The mixture was warmed to room temperature and stirred overnight. The mixture was filtered under nitrogen (medium glass frit), and the solvent evaporated from the clear yellow solution under vacuum to give a pale yellow solid. The compound was purified by vacuum sublimation (50° C. oil bath, 50 mtorr, <–5° C. cold-finger) overnight. A semi-crystalline white powder was obtained, 55.5 g, 77%. $^1$H NMR (C$_6$D$_6$): 3.38, 3.12 (m, 4H, CH$_2$CH$_2$), 1.18 (s, 18H, t-Bu). $^{13}$C NMR (C$_6$D$_6$): 55.77 (CR$_4$), 51.54 (CH$_2$CH$_2$), 31.48 (CH$_3$). Anal. Calcd for C$_{10}$H$_{22}$N$_2$SbCl: C, 36.67; H, 6.77; N, 8.55. Found: C, 36.71; H, 7.06; N, 8.58.

Example 2

Preparation of (tBuNCH$_2$CH$_2$NtBu)SbNMe$_2$

A solution of (tBuNCCNtBu)SbCl (15.00 g, 45 8 mmol) in diethylether (50 mL) was slowly added to an ice-cold suspension of lithium dimethylamide (2.34 g, 45.8 mmol) in diethylether (100 mL). The lithium amide dissolves then forms a fine white precipitate. The reaction mixture was warmed to room temperature and stirred overnight. The solvent was evaporated under vacuum, the grey residue extracted with pentane (100 mL), filtered under nitrogen (medium glass frit), and the solvent evaporated under vacuum to give a deep yellow oil. The oil was purified by fractional distillation (120° C. oil bath, <50 mtorr) collecting a clear and colorless liquid at 55° C. Yield: 12.1 g, 79%. $^1$H NMR (C$_6$D$_6$): 3.29, 2.96 (m, 4H, CH$_2$CH$_2$), 2.87 (s, 6H, NMe$_2$), 1.25 (s, 18H, t-Bu). $^{13}$C NMR (C$_6$D$_6$): 54.22 (CR$_4$), 50.16 (CH$_2$CH$_2$), 41.25 (NMe$_2$), 31.48 (CH$_3$). Anal. Calcd for C$_{12}$H$_{28}$N$_3$Sb: C, 42.88; H, 8.40; N, 12.50. Found: C, 42.78; H, 8.48; N, 12.46.

Example 3

Preparation of (tBuNCH$_2$CH$_2$NtBu)Sb(iPr)

A solution of isopropylmagnesium chloride (6.11 mL, 12.21 mmol, 2.0M in ether) was slowly added to an ice-cold solution of (tBuNCCNtBu)SbCl (4.00 g, 12.21 mmol) in diethylether (50 mL). A thick white solid formed. The reaction mixture was warmed to room temperature and stirred overnight. Pentane (50 mL) was added to the slurry and the mixture filtered under nitrogen (medium glass frit). The solvent was evaporated under vacuum to give a straw colored oil. The oil was purified by fractional distillation (100° C. oil bath, <50 mtorr) collecting a clear and colorless liquid at 52° C. Yield: 1.2 g, 29%. $^1$H NMR (C$_6$D$_6$): 3.18, 3.00 (m, 4H, CH$_2$CH$_2$), 1.64 (sept, 1H, iPr), 1.36 (d, 6H, $^3$J=7.5 Hz, iPr), 1.20 (s, 18H, tBu). $^{13}$C NMR (C$_6$D$_6$): 54.61 (tBuC), 53.51 (CH$_2$CH$_2$), 32.21 (tBu), 32.06, 23.01 (iPrCH), 20.23 (iPr). Anal. Calcd for C$_{13}$H$_{29}$N$_2$Sb: C, 46.59; H, 8.72; N, 8.36. Found: C, 46.44; H, 8.73; N, 8.39.

Example 4

Preparation of (tBuNCH$_2$CH$_2$NtBu)Sb(Me$_5$C$_5$)

A solution of (tBuNCCNtBu)SbCl (3.00 g, 9.16 mmol) in diethylether (20 mL) was slowly added to an ice-cold suspension of lithium pentamethylcyclopentadienyl (1.30 g, 9.16 mmol) in diethylether (50 mL) forming an orange precipitate. The reaction mixture was warmed to room temperature and stirred overnight. The solvent was evaporated under vacuum, the residue extracted with pentane (100 mL), filtered under nitrogen (medium glass frit), and the solvent evaporated under vacuum to give an orange powder. The solid was purified by sublimation (80° C. oil bath, <50 mtorr) collecting an orange crystalline solid. Yield: 2.7 g, 69%. Single-crystals were obtained from a saturated diethylether solution at −37° C. $^1$H NMR (C$_6$D$_6$): 3.19, 3.05 (m, 4H, CH$_2$CH$_2$), 2.19 (s, 15H, CH$_3$Cp), 1.18 (s, 18H, t-Bu). $^{13}$C NMR (C$_6$D$_6$): 121.84 (Cp), 55.38 (tBuC), 54.06 (CH$_2$CH$_2$), 32.45, 32.14? ((CH$_3$)$_3$C), 12.65 (CH$_3$Cp). Anal. Calcd for C$_{20}$H$_{37}$N$_2$Sb: C, 56.22; H, 8.73; N, 6.56. Found: C, 56.14; H, 8.67; N, 6.39.

Example 5

Preparation of (tBuNCH$_2$CH$_2$NtBu)Sb{Me$_2$NC(iPrN)$_2$}

N,N'-diisopropylcarbodiimide (1.93 g, 2.36 mL, 15.27 mmol) was slowly added to an ice-cold suspension of lithium dimethylamide (0.78 g, 15.27 mmol) in diethyl ether (50 mL). The resulting clear pale yellow solution was stirred at 0° C. for 3 hours. A solution of (tBuNCCNtBu)SbCl (5.00 g, 15.27 mmol) in diethylether (25 mL) was slowly added to the lithium guanidinate. A pale yellow precipitate formed upon addition. The reaction mixture was warmed to room temperature and stirred overnight. The solvent was evaporated under vacuum, the white residue extracted with pentane (100 mL), filtered under nitrogen (medium glass frit), and the solvent evaporated under vacuum to give a white powder. The compound was purified by sublimation (60° C. oil bath, <50 mtorr). Yield: 5.4 g, 77%. $^1$H NMR (C$_6$D$_6$): 4.0 (vbrs, 2H, iPrCH) 3.36, 3.17 (m, 4H, CH$_2$CH$_2$), 2.53 (s, 6H, NMe$_2$), 1.41 (s, 18H, t-Bu), 1.34 (brs, 12H, iPr). $^{13}$C NMR (C$_6$D$_6$): 100.86 (NCN), 54.83 (tBuC), 50.95 (CH$_2$CH$_2$), 41.85 (NMe$_2$), 31.75 (tBu), 31.45 (iPrCH), 26.17 (iPr). Anal. Calcd for C$_{19}$H$_{42}$N$_5$Sb: C, 49.36; H, 9.16; N, 15.15. Found: C, 49.41; H, 9.34; N, 14.93.

Example 6

Preparation of (tBuNCH$_2$CH$_2$NtBu)Sb{CH$_3$C(iPrN)$_2$}

A solution of methyl-lithium (28.6 mL, 45.8 mmol, 1.6M in hexanes) was slowly added to an ice-cold solution of N,N'-diisopropylcarbodiimide (5.78 g, 45.8 mmol) in diethyl ether (100 mL). The resulting clear and colorless solution was stirred at 0° C. for 3 hours. A solution of (tBuNCCNtBu)SbCl (15.0 g, 45.8 mmol) in diethylether (50 mL) was slowly added to the lithium amidinate. A fine white precipitate formed upon addition and solution phase turned yellow. The reaction mixture was warmed to room temperature and stirred overnight. The solvent was evaporated under vacuum, the yellow residue extracted with pentane (100 mL), filtered under nitrogen (medium glass frit), and the solvent evaporated under vacuum to give a yellow oil. The residue was triturated with diethylether (2×10 mL) and the solvent evaporated under vacuum. A yellow solid was obtained. The compound was purified by sublimation (70° C. oil bath, <50 mtorr, <−5° C. coolant coldfinger) to give a colorless crystalline solid. Yield: 11.8 g, 60%. $^1$H NMR (C$_6$D$_6$): 3.24 (m, 4H, CH$_2$CH$_2$), 1.74 (s, 3H, CH$_3$CN), 1.38 (s, 18H, tBu), 1.24 (d, $^3$J=6.6 Hz, iPr). $^{13}$C NMR (C$_6$D$_6$): 166 (NCN), 54.75 (CR$_4$), 51.12 (CH$_2$CH$_2$), 31.88 (iPrCH), 31.52 (tBu), 25.01 (iPr), 15.62 (CH$_3$CN). Anal. Calcd for C$_{18}$H$_{39}$N$_4$Sb: C, 49.90; H, 9.07; N, 12.93. Found: C, 49.73; H, 8.98; N, 12.87.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. An antimony precursor having one of the following formulae:

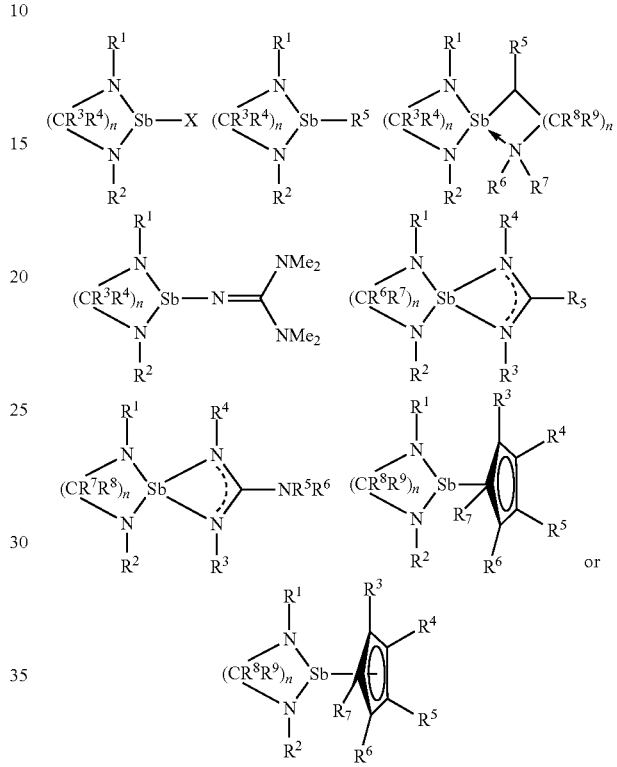

wherein:
each of R, R$^1$, R$^2$, R$^3$, R$^4$, R$^5$, R$^6$, R$^7$, R$^8$, and R$^9$ is the same as or different from others, and each is independently selected from H, halogen, C$_1$-C$_6$ alkyl, C$_1$-C$_6$ alkoxy, C$_3$-C$_8$ cycloalkyl, C$_6$-C$_{10}$ aryl, silyl, substituted silyl, amide, aminoalkyl, alkylamine, alkoxyalkyl, aryloxyalkyl, imidoalkyl and acetylalkyl;

X is the same as or different from others, and each is independently selected from H, halogen, C$_1$-C$_6$ alkyl, C$_1$-C$_6$ alkoxy, C$_3$-C$_8$ cycloalkyl, C$_6$-C$_{10}$ aryl, silyl, substituted silyl, amide, aminoalkyl, alkylamine, alkoxyalkyl, aryloxyalkyl, imidoalkyl and acetylalkyl, amidinate, guanidinate, isourate, cyclopentadienyl (C$_5$R$_5$); and n is an integer from 1 to 7.

2. The antimony precursor of claim 1, comprising an antimony bis-amide of the formula

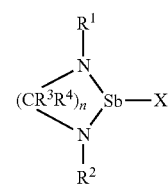

3. The antimony precursor of claim 1, comprising an antimony bis-amide of the formula.

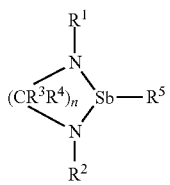

4. The antimony precursor of claim 1, comprising an antimony bis-amide of the formula

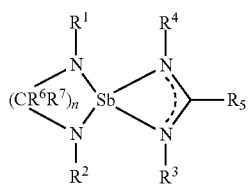

5. The antimony precursor of claim 1, comprising an antimony bis-amide of the formula

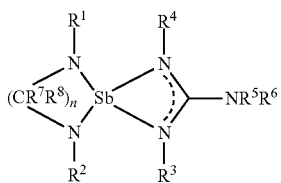

6. The antimony precursor of claim 1, comprising an antimony bis-amide of the formula

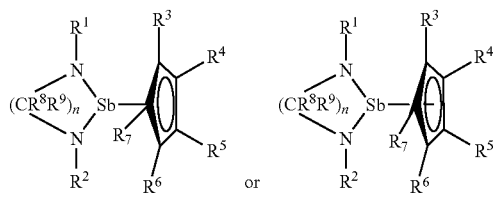

7. The antimony precursor of claim 1, comprising an antimony bis-amide of the formula

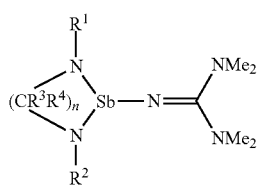

8. A composition comprising:
(a) an antimony precursor of claim 1; and
(b) a solvent medium in which said compound is dissolved.

9. The composition of claim 8, wherein the solvent medium comprises a hydrocarbon solvent.

10. The composition of claim 9, wherein the hydrocarbon solvent comprises one or more of alkanes, aromatics and amines.

11. The composition of claim 9, wherein the hydrocarbon solvent comprises one or more of hexane, heptane, octane, and pentane, benzene, toluene, triethylamine, and tert-butylamine.

12. A precursor vapor comprising vapor of an antimony precursor of claim 1.

13. The precursor vapor of claim 12, further comprising a co-reactant selected from the group consisting of $O_2$, $N_2O$, $H_2O$, ozone, $O_2$ plasma, hydrogen, $H_2$/plasma, amines, imines, hydrazines, silanes, germanes, ammonia, alkanes, alkenes, alkynes, boranes and compatible mixtures thereof, wherein the precursor vapor may be delivered simultaneously with the co-reactant or may be delivered in a pulsed manner wherein the precursor vapor and the co-reactant are temporarily separated.

14. A method of depositing an antimony-containing film on a substrate, comprising volatilizing an antimony precursor of claim 1 to form a precursor vapor, and contacting the substrate with the precursor vapor under deposition conditions to form the antimony-containing film on the substrate.

15. A method of forming a GST film on a substrate, comprising depositing antimony on the substrate from vapor of an antimony precursor of claim 1.

16. A method of making a PCRAM device, comprising forming a GST film on a substrate for fabrication of said device, wherein said forming comprises depositing antimony on the substrate from vapor of an antimony precursor of claim 1.

17. A method of forming an antimony-containing film on a substrate, comprising volatilizing precursor of claim 1 to form a precursor vapor, and contacting the precursor vapor with the substrate under atomic layer deposition or chemical vapor deposition conditions.

18. The method of claim 17, wherein the antimony-containing film is a GST film.

19. The method of claim 17, wherein the antimony-containing film is an amorphous GeTe film or an amorphous SbTe film.

20. A method of combating pre-reaction of a vapor phase precursor derived from a precursor of claim 1 in contact with a substrate for deposition of a film component thereon, comprising contacting said substrate, prior to said contact of the vapor phase precursor therewith, with a pre-reaction-combating agent selected from the group consisting of (i) heteroatom (O, N, S) organo Lewis base compounds, (ii) free radical inhibitors, and (iii) deuterium-containing reagents.

* * * * *

UNITED STATES PATENT AND TRADEMARK OFFICE
CERTIFICATE OF CORRECTION

PATENT NO. : 9,034,688 B2  
APPLICATION NO. : 14/217866  
DATED : May 19, 2015  
INVENTOR(S) : Tianniu Chen Page 1 of 1

It is certified that error appears in the above-identified patent and that said Letters Patent is hereby corrected as shown below:

In the Specification

Column 24, line 15: "45 8 mmol" should be -- 45.8 mmol --.

Signed and Sealed this  
Twenty-first Day of July, 2015

Michelle K. Lee  
*Director of the United States Patent and Trademark Office*